United States Patent

Pereira et al.

Patent Number: 5,023,348
Date of Patent: Jun. 11, 1991

[54] PROCESS FOR THE PREPARATION OF MACROLIDE COMPOUNDS

[75] Inventors: Oswy Z. Pereira, Hounslow; Michael V. J. Ramsay, South Harrow; Stephen Freeman, High Wycombe, all of United Kingdom

[73] Assignee: American Cyanamid Company, Me.

[21] Appl. No.: 504,030

[22] Filed: Apr. 2, 1990

Related U.S. Application Data

[63] Continuation of Ser. No. 242,158, Sep. 9, 1988, abandoned.

[30] Foreign Application Priority Data

Sep. 11, 1987 [GB] United Kingdom ............... 8721368
Sep. 11, 1987 [GB] United Kingdom ............... 8721369
Sep. 11, 1987 [GB] United Kingdom ............... 8721370

[51] Int. Cl.$^5$ ........................... C07D 313/00
[52] U.S. Cl. ........................................... 549/264
[58] Field of Search ................................. 549/264

[56] References Cited

U.S. PATENT DOCUMENTS 4,203,976 5/1980 Fisher et al. .................... 549/264
4,423,209 12/1983 Mrozik .............................. 549/264

Primary Examiner—C. Warren Ivy
Assistant Examiner—Amelia A. Owens
Attorney, Agent, or Firm—Bacon & Thomas

[57] ABSTRACT

A process for preparing a compound of formula (I)

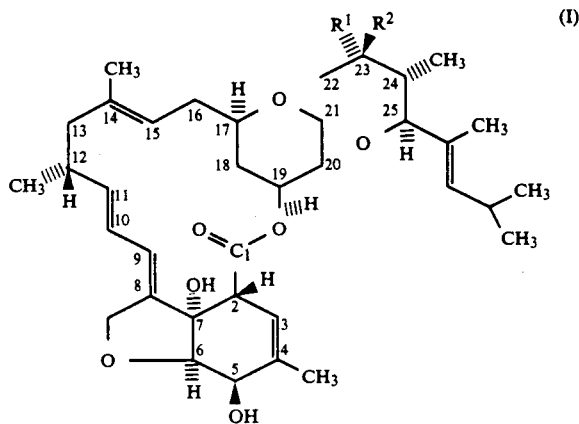

(where (i) $R^1$ is an ethoxy group and $R^2$ is a hydrogen atom, (ii) $R^1$ is a hydrogen atom and $R^2$ is a bromine atom or (iii) ($R^1$ and $R^2$ together with the carbon atom to which they are attached represent $>C=O$) which comprises stereoselectively reducing the corresponding 5-keto compound.

1 Claim, No Drawings

PROCESS FOR THE PREPARATION OF MACROLIDE COMPOUNDS

This application is a continuation of application Ser. No. 07/242,158, filed Sept. 9, 1988, now abandoned.

This invention relates to a novel process for the preparation of macrolide compounds of formula (I)

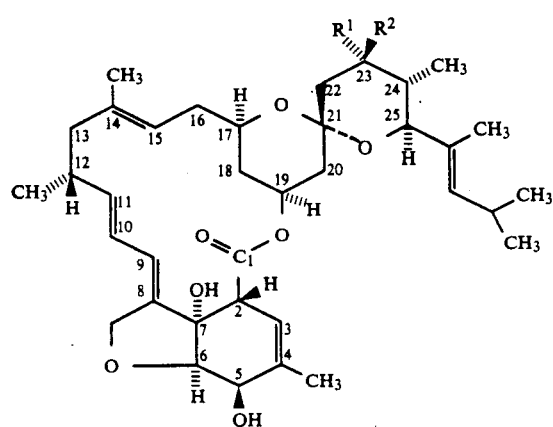

(where (i) $R^1$ is an ethoxy group and $R^2$ is a hydrogen atom, (ii) $R^1$ is a hydrogen atom and $R^2$ is a bromine atom or (iii) $R^1$ and $R^2$ together with the carbon atom to which they are attached represent $>C=O$). Compounds (i) and (iii) are described in GB-A No. 2176182 and have anti-endoparasitic, anti-ectoparasitic, anti-fungal, insecticidal, nematicidal and acaricidal activity and are useful in combating parasites in animals and humans and pests in agriculture, horticulture, forestry, public health and stored products. The compounds may also be used as intermediates in the preparation of other active compounds. The compound (ii) is also a useful intermediate and can for example be reduced with zinc to give the corresponding 23-desoxy compound.

The present invention provides a novel and useful two-step synthesis of the compounds of formula (I) from a fermented starting material. In particular, we describe the modification of the starting material to give an intermediate which is stereoselectively reduced to give the compound of formula (I). The overall process is convenient to use and provides the compound of formula (I) in good yield.

The key step in the two-step synthesis of the compound of formula (I) is the stereoselective reduction of the compound of formula (II)

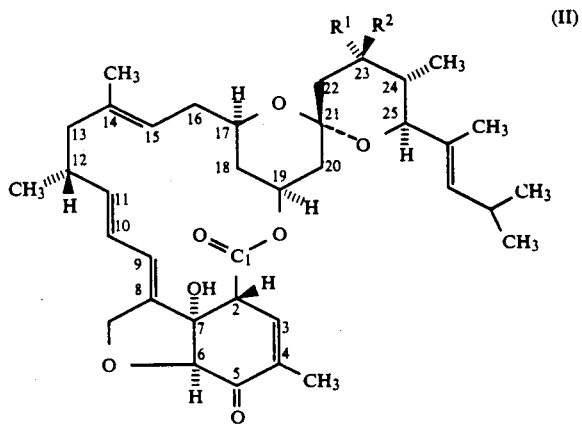

Thus, in one aspect of the present invention, we provide a process for preparing the compound of formula (I) which comprises reducing a compound of formula (II).

The reduction may be effected with a reducing agent which is capable of stereoselectively reducing the 5-keto group. Suitable reducing agents include borohydrides such as alkali metal borohydrides (e.g. sodium borohydride) and lithium alkoxyaluminium hydrides such as lithium tributoxyaluminium hydride.

The reaction involving a borohydride reducing agent takes place in the presence of a solvent such as an alkanol e.g. isopropyl alcohol or isobutyl alcohol conveniently at a temperature in the range of $-30°$ to $+80°$ C. e.g. at $0°$ C. The reaction involving a lithium alkoxyaluminium hydride takes place in the presence of a solvent such as an ether e.g. tetrahydrofuran or dioxan conveniently at a temperature in the range of $-78°$ to $0°$ C. e.g. at $-78°$ C.

The compound of formula (II) in which $R^1$ is an ethoxy group and $R^2$ is a hydrogen atom may be prepared by treating a compound of formula (III)

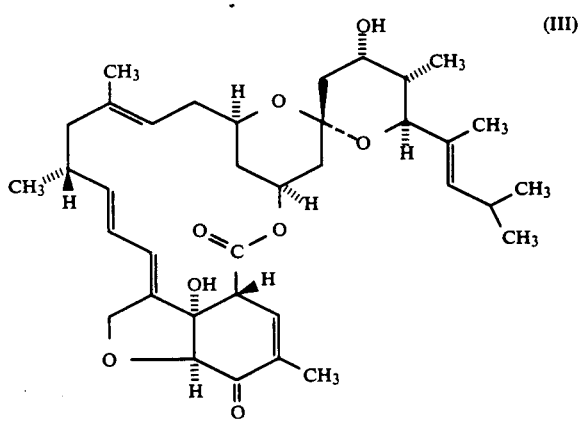

with a reagent of the formula $CH_3CH_2Y$ (where Y represents a leaving group such as a chlorine, bromine or iodine atom or a hydrocarbylsulphonyloxy group, such as mesyloxy or tosyloxy, or a haloalkanoyloxy group such as dichloroacetoxy).

The reaction may be effected in the presence of a silver salt such as silver oxide, silver perchlorate, silver carbonate or silver salicylate or mixtures thereof, and this system may be particularly appropriate when etherification is carried out using an ethyl halide (e.g. ethyl iodide).

Etherification may conveniently be effected in a solvent such as an ether e.g. diethyl ether.

The compound of formula (II) in which $R^1$ is a hydrogen atom and $R^2$ a bromine atom may be prepared by treating the compound of formula (III) with a suitable brominating agent.

The reaction may be effected with an brominating agent serving to replace the 23-OH group by a bromine atom with inversion of configuration, whereby a compound of formula (II) is produced. Suitable brominating systems include triarylphosphine (e.g. triphenylphosphine) and bromine in N,N-dimethylformamide.

The reaction is conveniently carried out in a co-solvent e.g. a nitrile such as acetonitrile at a temperature in the range of 0° to 50° C., conveniently at room temperature.

The compound of formula (II) in which $R^1$ and $R^2$ together with the carbon atom to which they are attached represent $>=0$ may be prepared by oxidising the compound of formula (III).

The reaction may be effected with an oxidising agent serving to convert a secondary hydroxyl group to an oxo group, whereby a compound of formula (II) is produced.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. sodium or pyridinium dichromate or chromium trioxide in pyridine preferably in the presence of a phase transfer catalyst; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicyclohexylcarbodiimide or an acyl halide, e.g. oxalyl choride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used. The choice of solvent will depend upon the type of oxidising agent used for the conversion.

The reaction may be carried out at a temperature of from −80° C. to +50° C.

The compound of formula (III) is described in GB-A No. 2187742 and may be prepared by cultivating *Streptomyces thermoarchaensis* NCIB 12015 or a mutant thereof and isolating the compound from the fermentation broth so obtained.

The Streptomyces organism may be cultured by conventional means, i.e. in the presence of assimilable sources of carbon, nitrogen and mineral salts. Assimilable sources of carbon, nitrogen and minerals may be provided by either simple or complex nutrients for example as described in UK Patent Specification No. 2166436.

Cultivation of the Streptomyces organism will generally be effected at a temperature of from 20° to 50° C. preferably from 25° to 40° C., and will desirably take place with aeration and agitation e.g. by shaking or stirring. The medium may initially be inoculated with a small quantity of a sporulated suspension of the microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 5.5 to 8.5.

The fermentation may be carried out for a period of 2–10 days, e.g. about 5 days.

The compound of formula (III) may be separated from the whole fermentation broth so obtained by conventional isolation and separation techniques. A variety of fractionation techniques may be used, for example adsorption-elution, precipitation, fractional crystallisation and solvent extraction which may be combined in various ways. Solvent extraction and chromatography have been found to be most suitable for isolating and separating the compound.

The invention is illustrated but not limited by the following Examples in which temperatures are in °C. and 'L' represents liter.

The compounds of formulae (I) and (II) are named hereinafter as derivatives of 'Factor A'. 'Factor A' is a compound of formula (I) in which $R^1$ is a hydroxy group and $R^2$ is a hydrogen atom.

Factor I is the compound of formula (III) above and its preparation is described in GB-A No. 2187742.

EXAMPLE 1

(i) 23-Desoxy-23-epi-bromo Factor I

Bromine (0.15 ml) was added dropwise to a stirred solution of triphenylphosphine (0.74 g) in dimethylformamide (2.6 ml) under nitrogen. The suspension was allowed to cool to room temperature and was diluted with ether. The solvent was decanted off and the solid was washed with ether. The dried solid was redissolved in acetonitrile (20 ml) and an aliquot (5 ml) was cooled in an ice bath and a solution of Factor I (100 mg) in acetonitrile (2 ml) was added under nitrogen. After 1 h the solution was allowed to warm to room temperature and the reaction was left for 20 h. The mixture was partitioned between ethyl acetate and 2N hydrochloric acid and the organic phase was separated. The organic phase was washed with 2N hydrochloric acid, then with saturated sodium bicarbonate solution, then was dried over sodium sulphate, and the solvent was evaporated. The residue was chromatographed over a column of silica (Merck Art 9385; 75 ml) made up in hexane (60°–80°)/ethyl acetate and eluted with the same solvent. Appropriate fractions of the major component were combined and the solvent was evaporated to leave the title compound as a foam (20 mg) $[\alpha]_D^{22}$ +4.3° (c 0.46; CHCl$_3$); $\lambda_{max}^{EtOH}$ 240 nm ($\epsilon$26,000); $\nu_{max}$ (CHBr$_3$) 3500 (OH), 1710 (ester), 1678 (ketone), 997 (C—O); $\delta$ (CDCl$_3$) include 0.95 (d;3H), 0.97 (d;3H), 1.00 (d;3H), 3.58 (m,1H), 4.19 (t;d;1H), 3.83 (s;1H), 3.85 (s;1H), and 6.58 (m;1H).

(ii) 23-Desoxy-23-epi-bromo Factor A (a) A stirred solution of 23-desoxy-23-epi-bromo Factor I (50 mg) in dry isopropanol (2 ml) was cooled to 0° under nitrogen and sodium borohydride (3 mg) was added. After 30 minutes the mixture was diluted with ether and 2N hydrochloric acid was added dropwise.

The organic phase was separated and was washed with 2N hydrochloric acid, dried over sodium sulphate and the solvent evaporated. The residue was chromatographed over a column of silica (Merck Art 9385; 50 ml) made up in hexane (60°-80°)/ethyl acetate (2:1) and eluted with the same solvent. Appropriate fractions of the major component were combined and the solvent was evaporated to leave the title compound as a foam (26 mg). $[\alpha]_D^{22}$ +71° (c 0.29; CHCl$_3$); $\lambda_{max}^{EtOH}$ 244.4 nm ($\epsilon$27,840); $\nu_{max}$ (CHBr$_3$) 3550, 3470 (OH), 1706 (ester), 993 (C—O); $\delta$ (CDCl$_3$) values include 0.93 (d;3H), 0.95 (d;3H), 1.00 (d;3H), 3.28 (m;1H), 3.90 (s;1H), 3.95 (s;1H), 4.19 (t;d;1H), 4.29 (t;1H), 5.42 (s;1H).

(b) A stirred solution of 23-desoxy-23-epi-bromo Factor I (50 mg) in dry tetrahydrofuran (5 ml) under nitrogen was cooled to ca −70°. Lithium tri-t-butoxyaluminohydride (110 mg) was added and after 1 h an additional portion of lithium tri-t-butoxyaluminohydride (95 mg) was added. After a further 1.5 h the reaction mixture was diluted with ethyl acetate and then aqueous 2N hydrochloric acid was added slowly. The organic phase was separated and was washed successively with 2N hydrochloric acid and saturated sodium bicarbonate solution and then dried over sodium sulphate. The solvent was evaporated to leave the title compound as a foam (53 mg).

EXAMPLE 2

23-Ethoxy Factor A (a) 23-Ethoxy Factor I

A solution of Factor I (350 mg) in dry ether (15 ml) was treated at 20°, under nitrogen, with silver carbonate (785 mg), iodoethane (0.27 ml) and silver perchlorate (590 mg). The resulting suspension was stirred for 64 h under nitrogen, diluted with ethyl acetate, washed with 2N-hydrochloric acid, water, and brine and dried. The residue was chromatographed over Kieselgel 60 eluting with light petroleum:ethyl acetate (4:1) to give a foam (202 mg).

A sample of the foam (20 mg) was crystallised from light petroleum (0.2 ml) to give the title compound as a colourless solid, m.p. 128°-130°, $[\alpha]_D^{21}$ +122° (c 0.43, CHCl$_3$).

(b) 23-Ethoxy Factor A (i) A solution of 23-ethoxy Factor I (40 mg) in isopropanol (3 ml) was stirred at 0° under nitrogen, and sodium borohydride (2.4 mg) was added. The resulting solution was stirred at 0° for 40 minutes, then diluted with ethyl acetate (25 ml), and 2N-hydrochloric aced (10 ml) was added, dropwise. The organic phase was washed with water, and brine (10 ml of each), and dried (magnesium sulphate), and evaporated to dryness. The residue (30 mg) was purified by chromatography over Kieselgel 60 (10 g). Elution of the column with light petroleum:ethyl acetate (2:1) gave the title compound (18 mg). $[\alpha]_D^{21}$ +178° (c 1.13, CHCl$_3$); $\lambda_{max}$ (EtOH) 244 nm ($\epsilon_{max}$ 29,400); $\delta$ (CDCl$_3$) include 4.29(t,7; 1H), 3.65(m;1H), 3.47(m;1H), 3.26(m;2H), 1.15(t,7; 3H).

(ii) A solution of 23-ethoxy Factor I (85 mg) in dry tetrahydrofuran (2 ml), under nitrogen, was cooled to −78° and treated with a solution of lithium tri-tert-butoxy alumino hydride (396 mg) in dry tetrahydrofuran (7 ml). After 5 h at −78° the pale yellow solution was partitioned between ether:2N hydrochloric acid (2:1, 60 ml). The organic phase was washed with water (30 ml) and brine, and then dried and evaporated to a foam (85 mg). A solution of the foam in hexane:ethyl acetate (3:1) was applied to a column of Merck Kieselgel 230–400 mesh silica (16 g) and eluted, under pressure, with the same solvent system to give the title compound as a white foam (52 mg). The product obtained was spectroscopically similar to the compound prepared according to Example 2(b) (i).

EXAMPLE 3

23-Keto Factor A (a) 5,23-Diketo Factor A

An ice-cold solution prepared from concentrated sulphuric acid (1.2 ml) and sodium dichromate (120 mg) in water (2 ml) was added over 15 min to an ice-cold solution of 5-keto Factor A (200 mg) and tetrabutylammonium hydrogen sulphate (15 mg) in ethyl acetate (4 ml) with vigorous stirring. After 1 h the mixture was diluted with ethyl acetate and the organic phase was washed with saturated aqueous sodium bicarbonate. The dried organic phase was evaporated and the gum was purified by chromatography over Merck Keiselgel 60 230–400 mesh (100 ml). Elution with 10% ethyl acetate in dichloromethane afforded the title compound as a pale yellow foam (86 mg) $\delta$ (CDCl$_3$) includes 6.57 (m,1H); 2.50 (s,2H); and 1.89 (m,3H).

(b) 23-Keto Factor A

Sodium borohydride (30 mg) was added to an ice-cold solution of 5,23-diketo Factor A (402 mg) in isopropanol (50 ml). The mixture was stirred in an ice bath for 50 min, diluted with ethyl acetate (150 ml) and washed successively with 1N hydrochloric acid, water and brine. The dried organic phase was evaporated and the yellow foam was purified by chromatography over Merck Kieselgel 60 230–400 mesh (150 ml). Elution of the column with hexane:ethyl acetate (2:1) afforded the title compound as a pale yellow foam (169 mg) $[\alpha]_D^{21}$ +144° (c 1.20, CHCl$_3$), $\lambda_{max}$ (EtOH) 244 nm ($\epsilon$26.000), $\delta$ (CDCl$_3$) includes 3.28 (m;1H), 3.48 (m;1H), 3.70 (d10; 1H) and 4.28 (t7; 1H).

We claim:

1. A process for preparing a compound of formula (I)

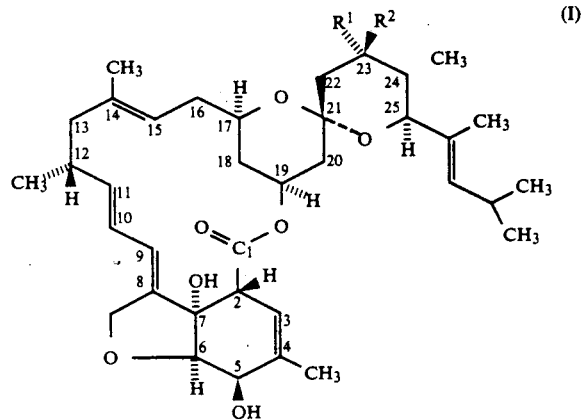

where (i) R$^1$ is an ethoxy group and R$^2$ is a hydrogen atom, (ii) R$^1$ is a hydrogen atom and R$^2$ is a bromine atom, or (iii) R$^1$ and R$^2$ together with the carbon atom to which they are attached represent >C=O, which comprises stereoselectively reducing the corresponding compound of formula (II)
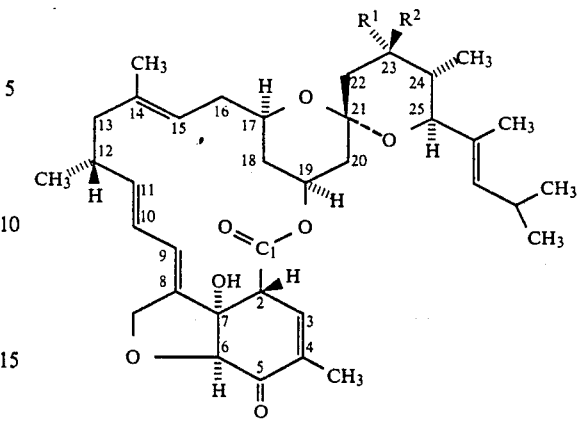
wherein the reduction is effected with sodium borohydride or lithium tributoxyaluminum hydride.
* * * * *